US010485644B2

(12) United States Patent
Orr et al.

(10) Patent No.: US 10,485,644 B2
(45) Date of Patent: Nov. 26, 2019

(54) INSERTER FOR URETHRAL PLUG (71) Applicant: Life360 Innovations Inc., Vancouver (CA)

(72) Inventors: Robert Mitchell Orr, Vancouver (CA); Thom Bellaire, Vancouver (CA); Nigel Halsted, Vancouver (CA); Ernie Janzen, Vancouver (CA); Nicole Ranger, Vancouver (CA)

(73) Assignee: LIFE360 INNOVATIONS INC., Vancouver, BC (CA)

( * ) Notice: Subject to any disclaimer, the term of this patent is extended or adjusted under 35 U.S.C. 154(b) by 215 days.

(21) Appl. No.: 15/683,167

(22) Filed: Aug. 22, 2017

(65) Prior Publication Data
US 2019/0060046 A1   Feb. 28, 2019

(51) Int. Cl.
A61F 2/00        (2006.01)
A61F 13/26       (2006.01)
A61F 13/84       (2006.01)
A61B 17/12       (2006.01)

(52) U.S. Cl.
CPC ...... A61F 2/0009 (2013.01); A61B 17/12159 (2013.01); A61F 2/0004 (2013.01); A61F 13/266 (2013.01); A61F 13/84 (2013.01); A61B 2017/1205 (2013.01)

(58) Field of Classification Search
CPC ...... A61F 2/0009; A61F 2/0004; A61F 13/84; A61F 13/266
USPC ..................................... 600/29-32
See application file for complete search history.

(56) References Cited

U.S. PATENT DOCUMENTS

| | | | |
|---|---|---|---|
| 2,649,854 A | 8/1953 | Salm |
| 2,848,998 A | 8/1958 | Bryan |
| 3,463,141 A | 8/1969 | Mozolf |
| 3,648,683 A | 3/1972 | Brodie |
| 4,457,299 A | 7/1984 | Cornwell |
| 4,934,999 A | 6/1990 | Bader |
| 5,090,424 A | 2/1992 | Simon et al. |
| 5,140,999 A | 8/1992 | Ardito |
| 5,479,945 A | 1/1996 | Simon |
| 5,498,252 A | 3/1996 | Silber |

(Continued)

FOREIGN PATENT DOCUMENTS

| | | |
|---|---|---|
| DE | 10304614 A1 | 8/2004 |
| EP | 0193406 A2 | 9/1986 |

(Continued)

OTHER PUBLICATIONS

Dribblestop Product information downloaded from http://www.incontinenceclamp.com/product.php?gclid=CLHvua-Wj6UCFRhzgwodlwx5Mg on Jul. 11, 2010; 1 page.

(Continued)

Primary Examiner — John P Lacyk
(74) Attorney, Agent, or Firm — Schwabe Williamson & Wyatt, PC (57) ABSTRACT A urethral plug inserter for insertion a urethral plug into a urethra of a male subject. The device including: a proximal insertion end; a distal gripping end; a central portion disposed between the proximal insertion end and the distal gripping end; and a central channel comprising a floor and axially extending from the proximal insertion end to the distal gripping end and configured to accept a lanyard section of the urethral plug.

29 Claims, 8 Drawing Sheets

(56) References Cited

U.S. PATENT DOCUMENTS

| | | | |
|---|---|---|---|
| 5,509,427 | A | 4/1996 | Simon |
| 5,513,659 | A | 5/1996 | Buuck |
| 5,630,429 | A | 5/1997 | Dann |
| 5,671,755 | A | 9/1997 | Simon |
| 5,701,914 | A | 12/1997 | Loeffler |
| 5,752,525 | A | 5/1998 | Simon et al. |
| 5,759,194 | A | 6/1998 | Hammerslag |
| 5,884,629 | A | 3/1999 | O'Brien |
| 5,906,575 | A | 5/1999 | Conway |
| 5,954,688 | A | 9/1999 | Adams |
| 5,971,967 | A | 10/1999 | Willard |
| 5,989,230 | A | 11/1999 | Frassica |
| 6,080,142 | A | 6/2000 | Sachse |
| 6,558,370 | B2 | 5/2003 | Moser |
| 6,695,763 | B2 | 2/2004 | Zunker et al. |
| 6,911,001 | B2 | 6/2005 | Zunker |
| 7,108,655 | B2 | 9/2006 | Whalen et al. |
| 7,255,673 | B2 | 8/2007 | Ulmsten |
| 7,655,021 | B2 | 2/2010 | Brasington et al. |
| 7,771,344 | B2 | 8/2010 | Ziv |
| 9,707,065 | B2 | 7/2017 | Kunz |
| 2003/0125603 | A1 | 7/2003 | Zunker |
| 2003/0213494 | A1 | 11/2003 | Tihon |
| 2003/0229263 | A1* | 12/2003 | Connors ............... A61B 5/205 600/29 |
| 2004/0122285 | A1 | 6/2004 | Zunker |
| 2006/0079835 | A1 | 4/2006 | Frassica |
| 2006/0195006 | A1 | 8/2006 | Daurell et al. |
| 2007/0078389 | A1 | 4/2007 | Whalen et al. |
| 2008/0009931 | A1 | 1/2008 | Bartning et al. |
| 2009/0203959 | A1 | 8/2009 | Ziv |
| 2011/0028778 | A1 | 2/2011 | Kunz |
| 2013/0253260 | A1 | 9/2013 | Lund |

FOREIGN PATENT DOCUMENTS

| | | |
|---|---|---|
| EP | 082191 A2 | 2/1998 |
| WO | 92/19192 A1 | 11/1992 |
| WO | 2008067557 A2 | 6/2008 |
| WO | 2012083159 A2 | 6/2012 |

OTHER PUBLICATIONS

Datamonitor, "Pipeline and Commercial Insight: Urinary Incontinence," 185 pages, published Dec. 2007.

Supplemental European Search Report in EP App. No. 18849349 dated Aug. 16, 2019; 4 pages.

* cited by examiner

INSERTER FOR URETHRAL PLUG

CROSS REFERENCE TO RELATED APPLICATIONS

The present application is related to U.S. patent application Ser. No. 15/683,124, filed Aug. 22, 2017, entitled "Urethral Plug and System for Addressing Urinary Incontinence," the entire disclosure of which is hereby incorporated by reference in its entirety.

TECHNICAL FIELD

The present disclosure relates to a device for the insertion into the urethra of a urethral plug for controlling or mitigating urinary leakage and the methods associated with the use of same.

BACKGROUND

Urinary incontinence, or the loss of bladder control, is a common and potentially embarrassing problem. Urinary incontinence is not just a medical problem; it can affect emotional, psychological and social life. Many people who have urinary incontinence are afraid to conduct normal daily activities. The common ways to deal with urinary incontinence include collecting systems, absorbent products, fixed-occlusion devices, and indwelling catheters.

Absorbent products (including shields, undergarments, protective underwear, briefs, diapers, adult diapers, and underpants) are the best known product types to manage incontinence. They are generally easy to acquire in pharmacies or supermarkets. The disadvantages with absorbent products are that they can be bulky, leak, have odors, and can cause skin breakdown.

Collecting systems typically consist of a sheath worn over the penis funneling the urine into a urine bag worn on the leg. These products come in a variety of materials and sizes for individual fit. The disadvantages of these products are that it is necessary to get measured to ensure proper fit and you need a health care professional to write a prescription for them.

Fixed-occlusion devices (for men) are strapped around the penis, softly pressing the urethra and stopping the flow of urine. This management solution is only suitable for light or moderate incontinence.

Indwelling catheters (also known as Foley catheters) are very often used in hospital settings or if the user is not able to handle any of the above solutions. The indwelling catheter is typically connected to a urine bag that can be worn on the leg or hang on the side of the bed. Indwelling catheters need to be changed on a regular basis by a health care professional. The disadvantage, however, is that it is very common to get urinary tract infections when using indwelling catheters.

Intermittent catheters are single use catheters that are inserted into the bladder to empty it, and once the bladder is empty they are removed and discarded. Intermittent catheters are primarily used for retention (inability to empty the bladder) but for some people can be used to reduce/avoid incontinence.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

In the following detailed description, reference is made to the accompanying drawings, which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Globally, up to 35% of the population over the age of 60 years is estimated to be incontinent. It has been estimated that twenty-four percent of older adults in the U.S. have moderate or severe urinary incontinence that should be treated medically. Bladder control problems have been found to be associated with higher incidence of many other health problems such as obesity and diabetes. Difficulty with bladder control results in higher rates of depression and limited activity levels. Incontinence is expensive both to individuals in the form of bladder control products and to the health care system and nursing home industry. Injury related to incontinence is a leading cause of admission to assisted living and nursing care facilities. Both women and men can become incontinent from neurologic injury, congenital defects, strokes, multiple sclerosis, and physical problems associated with aging.

Men tend to experience incontinence less often than women, and the structure of the male urinary tract accounts for this difference. However, urinary incontinence is common in males having undergone prostate cancer treatments, for example surgical resection and/or radiation treatment. While urinary incontinence affects older men more often than younger men, the onset of incontinence can happen at any age. Estimates in the mid-2000s suggested that 17 percent of men over age 60, an estimated 600,000 men, experienced urinary incontinence, with this percentage increasing with age.

As disclosed in co-pending U.S. patent application Ser. No. 15/683,124, filed Aug. 22, 2017, entitled "Urethral Plug and System for Addressing Urinary Incontinence," a urethral plug has been developed that controls or mitigates urinary leakage associated with urinary incontinence. The device is configured so that optimally it only needs to be removed for the user to void their bladder. The device is simple in design and can be inserted using a disclosed inserter by the user without any assistance from others.

Embodiments of the present disclosure relate to a device inserting a urethral plug, such as a urethral plug disclosed in co-pending U.S. patent application Ser. No. 15/683,124, filed Aug. 22, 2017, entitled "Urethral Plug and System for Addressing Urinary Incontinence." In various embodiments, the urethral plug inserter includes a proximal insertion end, a distal gripping end, and a central portion (shaft) disposed between the proximal insertion end and the distal gripping end. The main body of the inserter is elongate, such as a substantially cylindrical tubular structure, although other cross-sectional shapes, such as ovoid, are contemplated. In embodiments, the distal gripping end includes protruding ridges on an exterior surface that are configured to provide a grip for a user. Placement and/or insertion of the urethral plug inserter is performed by gripping the gripping end of the inserter with a urethral plug coupled thereto, placing the insertion end at the entrance to the urethra, and pushing the inserter into the urethra a desired depth to place the urethral plug in the wearer's urethra. Entry of the inserter intro the urethral opening is facilitated by the shape of the urethral plug. In embodiments, the urethral plug inserter further includes a central channel that axially extends from the proximal insertion end to the distal gripping end and is configured to accept a lanyard section of a urethral plug. In embodiments, the central channel is generally U shaped with a curved bottom or floor and straight walls extending from the bottom. The edges of the central channel may be slightly rounded or chamfered to aid in the ease of aligning the urethral plug in the central channel.

In certain embodiments, the floor of the central channel slopes upward, both from the distal gripping end and the proximal insertion end, toward a middle of the central portion. As the central channel slopes, the depth of the central channel is less in the middle of the central portion than the depth of the central channel at the distal gripping end and the proximal insertion end. In embodiments, the slope is configured such that a lanyard of the urethral plug creates a smooth, essentially contiguous surface with the outer surface of the inserter in the middle of the central portion. The urethral plug and the central portion form this essentially contiguous surface for a length of about 6-12 cm, such as about 8-10 cm. In embodiments, at its shallowest, the depth of the channel is about 1-2 mm, whereas the channel is about 3-4 mm at its deepest location. This configuration provides comfort as the urethral plug insertion device, and urethral plug coupled thereto, are inserted into the urethra of a wearer. This configuration also facilitates the separation of the urethral plug from the urethral plug insertion device once appropriately placed in the urethra.

In embodiments, the proximal insertion end comprises a tapered conic section contiguous with the central channel. This tapered conic section is configured to match the contour of, and thereby retain, the urethral plug. This configuration provides for enhanced coupling of the urethral plug to the urethral plug insertion device, for example, so the urethral plug does not become dislodged during insertion in the wearer's urethra. In embodiments, the tapered conic section makes an angle with respect to the outside of the urethral plug insertion device from about 25° to about 35°.

In embodiments, the distal gripping end includes a urethral plug stopper retention system. The urethral plug stopper retention system includes a first set of urethral plug location protrusions and a second set of urethral plug location protrusions separated by, and disposed on either side of, a urethral plug stopper location slot. The configuration provides a groove for a stopper or handle of a urethral plug to seat. In combination with the conic section in the insertion end of the device and the central channel, the retention system holds the urethral plug in place by application of a slight amount of tension to the lanyard portion of the urethral plug. In embodiments, the first urethral plug location protrusion protrudes further than the second urethral plug location protrusions. In embodiments about 500+/−150 grams of force are applied to pass the stopper over the first urethral plug location protrusion, and the lanyard is maintained under about 300+/−100 grams of tension when seated in the central channel.

In embodiments, the inserter has a smooth outer surface. In certain embodiments, the inserter has a surface finish designation from about A-2 to about C-1 as set forth in the SPI guidelines for surface finish, for example the inserter has a surface finish designation of A2, A3, B-1, B-2, B-3, or C-1. In a specific embodiment, the inserter has a surface finish designation of B-1.

In some embodiments, the central portion (shaft) comprises two or more depth indicators, configured to provide information about the insertion depth of the urethral plug inserter in the urethra of the male subject. The depth indicators are spaced on the outside surface of the central portion and may be used by the wearer of the urethral plug as a guide for depth placement of the urethral plug.

In embodiments, the proximal insertion end, the distal gripping end, and the central portion comprise a polymer or blend of polymers. In embodiments, the inserter comprises a styrene butadiene copolymer (SBC). In specific embodiments, the inserted comprises K-Resin®. In embodiments, the inserter has an outer surface comprising a biologically inert material.

In embodiments, the proximal insertion end, the distal gripping end, and the central portion are a unitary body of continuous material, such as formed by a molding process or another formation process.

In embodiments, the inserter is substantially rigid, and does not bend or flex during use. Alternatively, a desired amount of flexibility may be permitted in the inserter.

In embodiments, the inserter has a fixed maximum diameter of 3 to 15 mm. In embodiments, the inserter has a fixed maximum length of about 100 to about 130 mm.

In embodiments, the inserter may be configured for re-use or may be configured for single use.

Figure 1A:
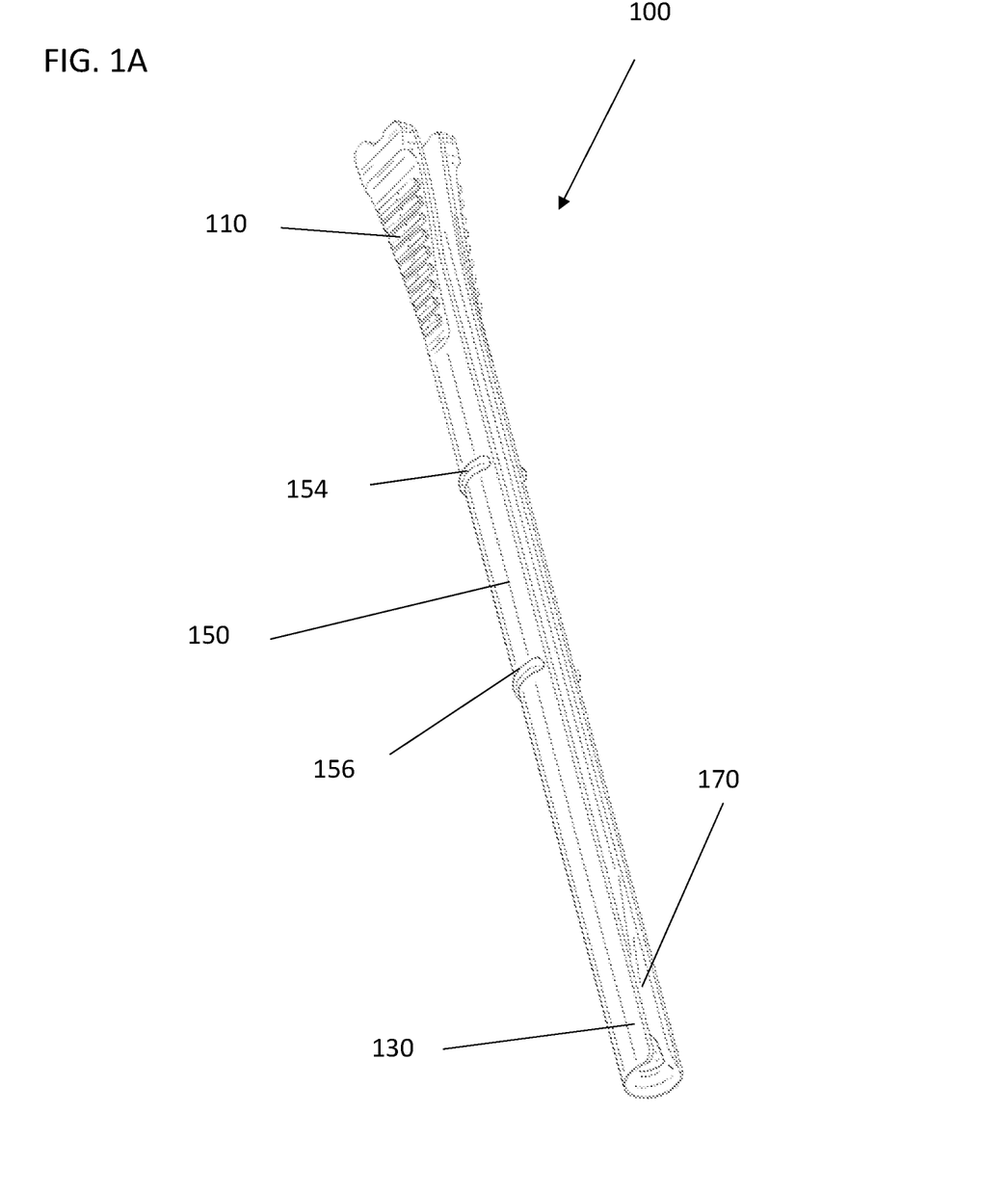
FIG. 1A is a perspective view of an inserter for a urethral plug, in accordance with disclosed embodiments.
Figure 1B:
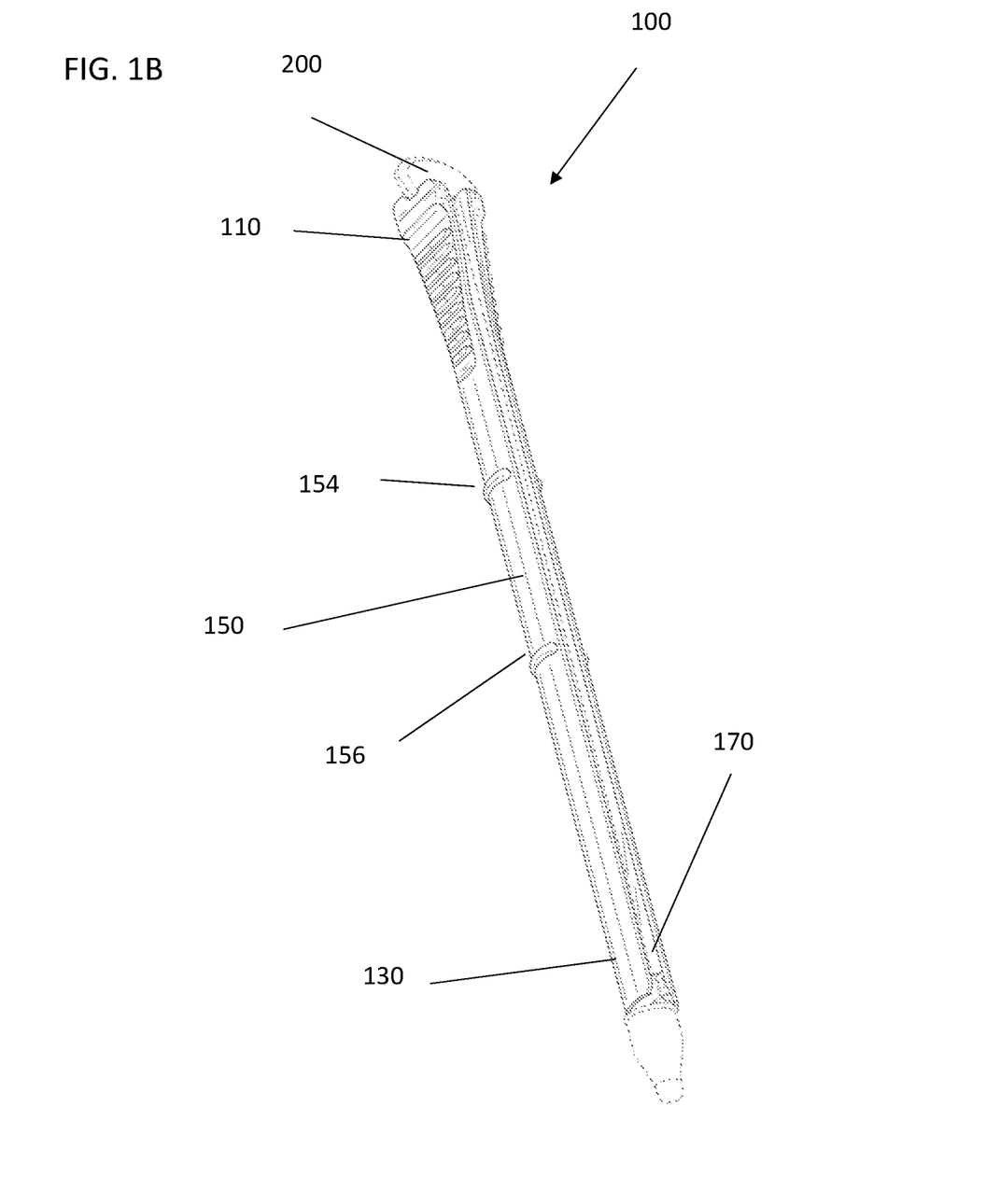
FIG. 1B is a perspective view of the inserter for a urethral plug with a urethral plug coupled thereto, in accordance with disclosed embodiments.

With reference to FIGS. 1A-1B an exemplary urethral plug insertion device 100 is provided. FIG. 1A shows a perspective view of a urethral plug insertion device 100, in accordance with disclosed embodiments. FIG. 1B shows a perspective view of the urethral plug insertion device 100 of FIG. 1A with a urethral plug 200 coupled thereto, in accordance with disclosed embodiments. The urethral plug insertion device 100 includes a proximal (to the urethra) insertion end 130, a distal gripping end 110, and a central portion (shaft) 150 disposed between the proximal insertion end 130 and the distal gripping end 110.

The central portion 150 includes depth indicators 154 and 156 as ridges on the central portion 150. The depth indicators 154 and 156 are spaced on the central portion 150 and may be used by the wearer of the urethral plug 200 as a guide for depth placement of the urethral plug 200. For example, when inserted, the urethral plug insertion device 100 may be inserted into the urethra to a depth between depth indicators 154 and 156 to insure proper placement of the urethral plug 200. By way of example, when properly inserted in the urethra, depth indicator 156 may be inside the urethra while depth indicator 154 may remain outside the urethra. In embodiments, 1, 2 or more than 2 depth indicators may be used, while in other embodiments there may be no depth indicators.

The urethral plug insertion device 100 further includes a central channel 170 running axial from the proximal insertion end 130 to the distal gripping end 110. The features of the central channel 170 will be discussed in greater detail below.

Figure 2A:
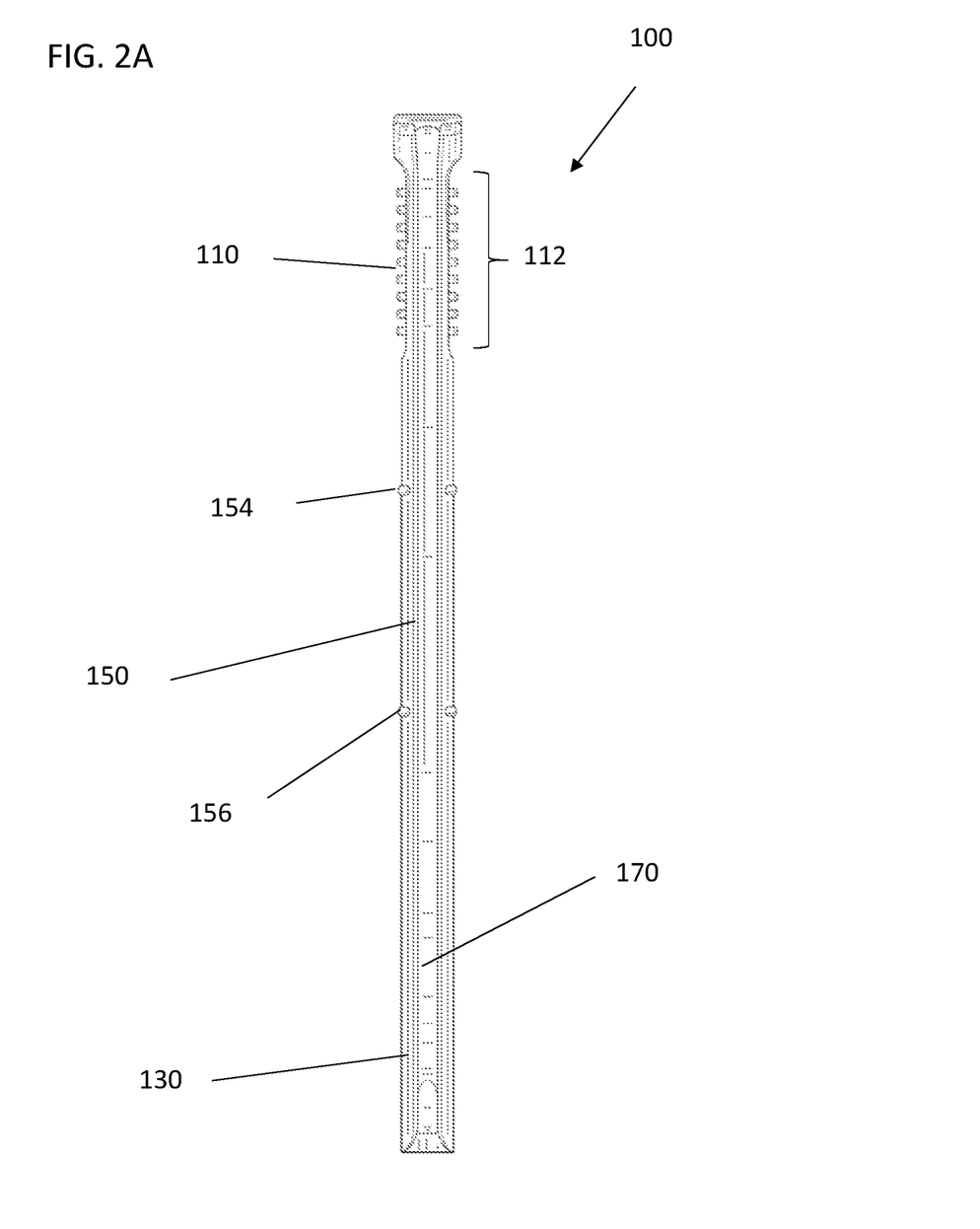
FIG. 2A is top view of the inserter for a urethral plug, in accordance with disclosed embodiments.
Figure 2B:
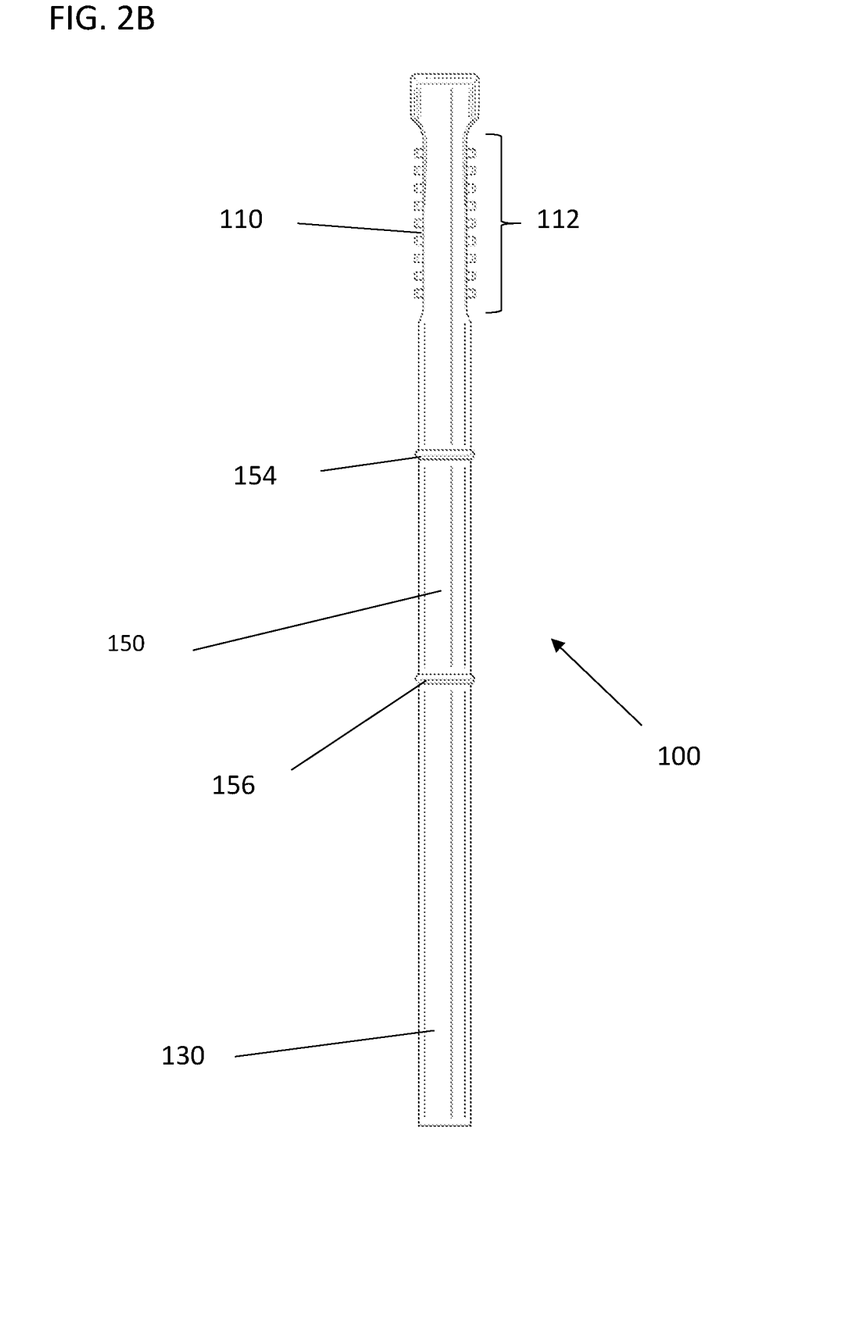
FIG. 2B is back view of the inserter for a urethral plug, in accordance with disclosed embodiments.

FIG. 2A shows a top view (as viewed facing the central channel 170) of the urethral plug insertion device 100, in accordance with disclosed embodiments. FIG. 2B shows a back view of the urethral plug insertion device 100, in accordance with disclosed embodiments. These views show details of the distal gripping end 110 of the urethral plug insertion device 100, including raised ribs 112 that are configured to allow a good grip, such with the thumb and index finger, on the distal gripping end 110 of the urethral plug insertion device 100.

Figure 3:
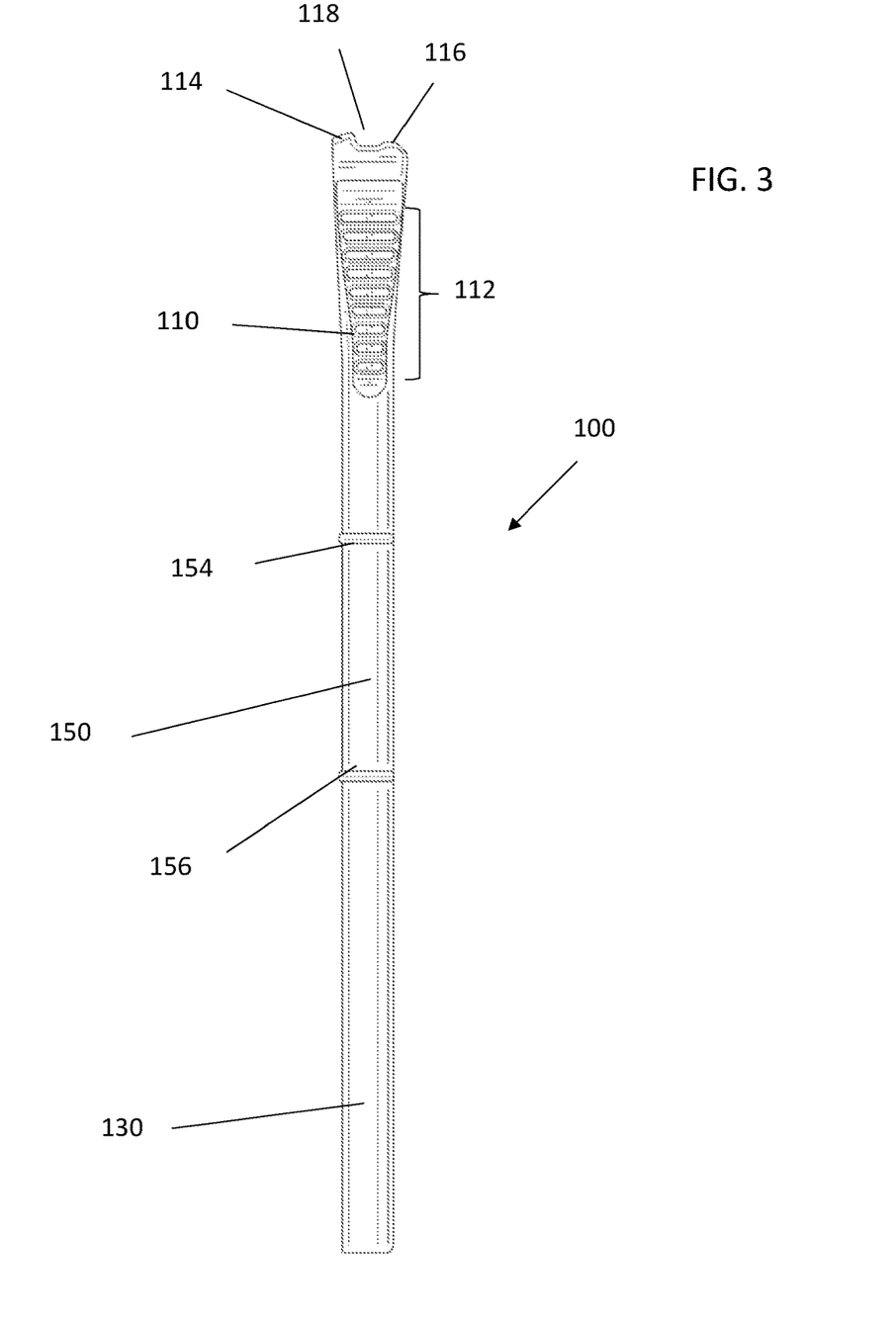
FIG. 3 is a side view of the inserter for a urethral plug, in accordance with disclosed embodiments.

FIG. 3 shows a side view of the urethral plug insertion device 100, in accordance with disclosed embodiments. In this view, additional features of the distal gripping end 110 of the urethral plug insertion device 100 are shown. As shown in the view, the distal gripping end 110 includes first urethral plug location protrusions 114 and second urethral plug location protrusions 116 separated by, and disposed on either side of, a urethral plug location slot 118. The plug location protrusions 114 and 116 and the urethral plug location slot 118 work in concert to hold a urethral plug (such as shown in FIG. 1B) in the correct position for insertion into the urethra of a wearer. The first urethral plug location protrusion 114 is located on the side opposite the central channel 170 while the second urethral plug location protrusions 116 are located on the side adjacent to the central channel 170. In addition, the first urethral plug location protrusion 114 protrudes further than the second urethral plug location protrusions 116. This works to bias the release of the urethral plug to the central channel 170 side of the urethral plug insertion device 100. In addition, the low profile of the second urethral plug location protrusions 116 facilitates coupling of the urethral plug to the central channel 170 side of the urethral plug insertion device 100.

Figure 4:
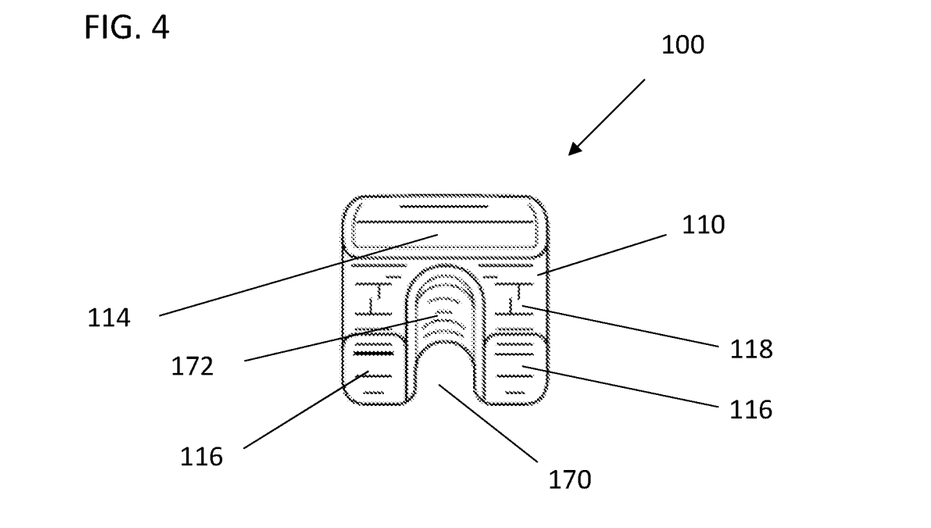
FIG. 4 is an end view of the inserter for a urethral plug as viewed from the gripping end, in accordance with disclosed embodiments.

FIG. 4 shows an end view of the urethral plug insertion device 100 as viewed from the distal gripping end 110, in accordance with disclosed embodiments. In this view, the positions of the first urethral plug location protrusion 114, the second urethral plug location protrusions 116, and the urethral plug location slot 118 can be clearly seen. It is also clear that the second urethral plug location protrusions 116 are composed of two protrusions on opposite sides of the central channel 170. Also visible in this view is the floor 172 of the central channel 170. The floor 172 of the central channel 170 is generally U shaped with a round bottom and straight walls extending from the bottom. The edges of the central channel 170 may also be slightly chamfered to aid in the ease of seeding the urethral plug in to the central channel 170. An important feature of the floor 172 of the central channel 170 is also shown. The floor 172 of the central channel slopes upward from the distal gripping end 110 of the urethral plug insertion device 100. This slope is configured such that the lanyard of the urethral plug creates a smooth essentially contiguous surface with the urethral plug insertion device 100 in the middle of the central portion 150. This configuration provides comfort as the urethral plug insertion device 100 and urethral plug coupled thereto is inserted into the urethra of a wearer. This configuration also aids in separation of the urethral plug from the urethral plug insertion device 100 once appropriately placed in the urethra.

Figure 5:
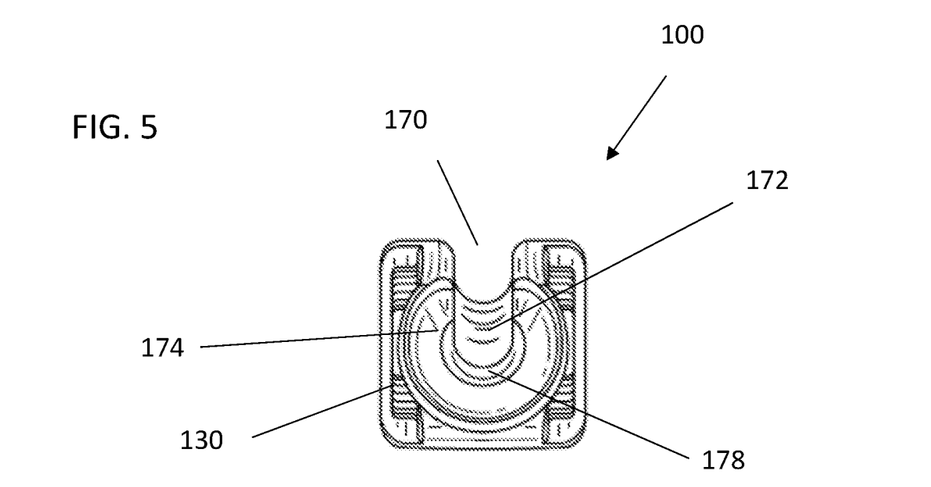
FIG. 5 is an end view of the inserter for a urethral plug as viewed from the insertion end, in accordance with disclosed embodiments.

FIG. 5 shows an end view of a urethral plug insertion device 100 as viewed from the proximal insertion end 130, in accordance with disclosed embodiments. Several features of the proximal insertion end 130 can be seen in this view. Visible in this view is the floor 172 of the central channel 170. As was shown in FIG. 4, the floor 172 of the central channel 170 is generally U shaped with a round bottom and straight walls extending from the bottom. The edges of the central channel 170 may also be slightly chamfered to aid in the ease of seeding the urethral plug in to the central channel 170. As with the distal gripping end 110, the floor 172 of the central channel slopes upward from the proximal insertion end 110 of the urethral plug insertion device 100. Also shown in this view are the plug body coupling taper 174. The coupling taper 174 is a conic section configured to approximately match the contour of the plug body of the urethral plug, such as shown in FIG. 1B. This configuration provides for enhanced coupling of the urethral plug to the urethral plug insertion device 100, for example so the urethral plug does not become dislodged during insertion in the wearer's urethra.

Figure 6:
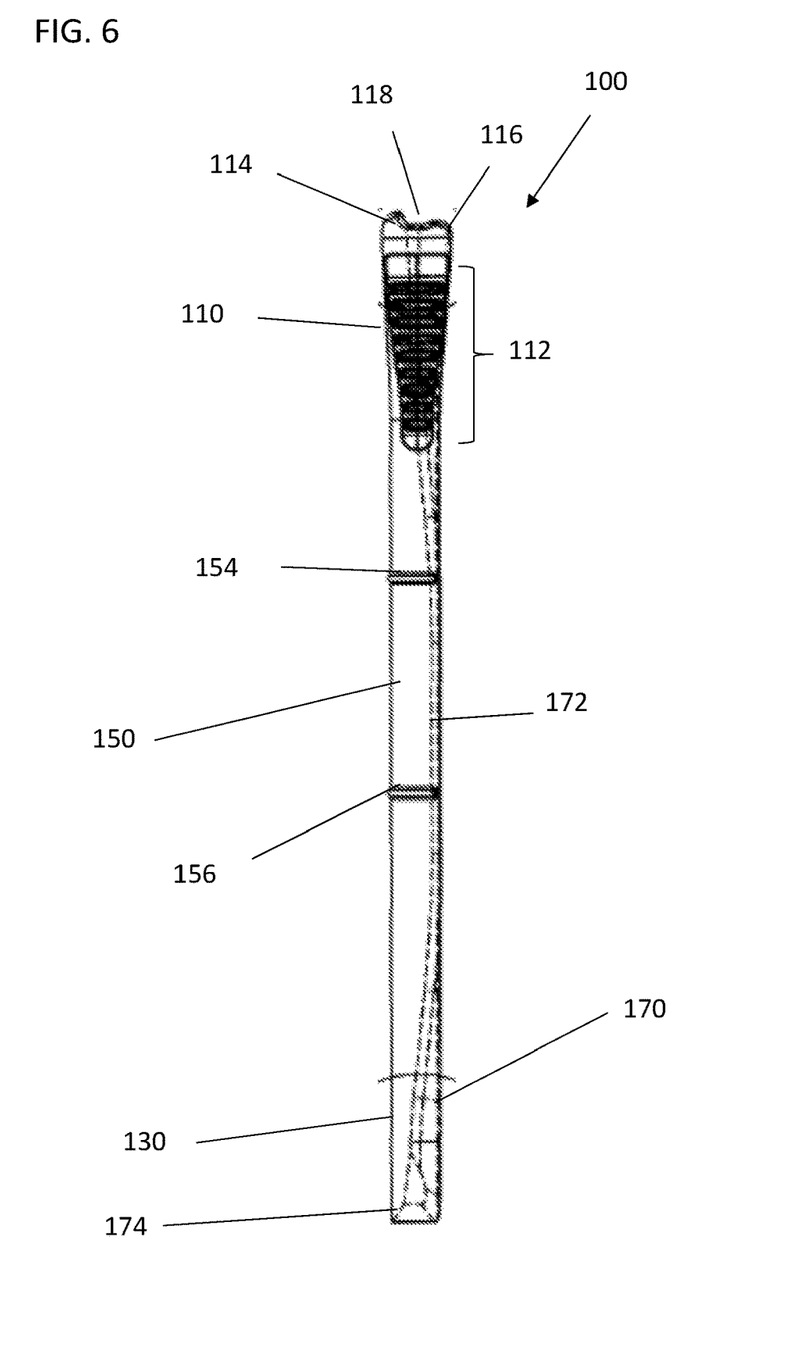
FIG. 6 is a transparent side view of the inserter for a urethral plug, in accordance with disclosed embodiments.

FIG. 6 shows a transparent side view of the urethral plug insertion device 100, in accordance with disclosed embodiments. In this view the contour of the floor 172 of the central channel 170 and the coupling taper 174 can be clearly seen. The floor 172 of the central channel slopes upward from both the proximal insertion end 130 and the distal gripping end 110 of the urethral plug insertion device 100. This slope is configured such that the lanyard of the urethral plug creates a smooth essentially contiguous surface with the urethral plug insertion device 100. Also shown in this view are the plug body coupling taper 174.

Figure 7:
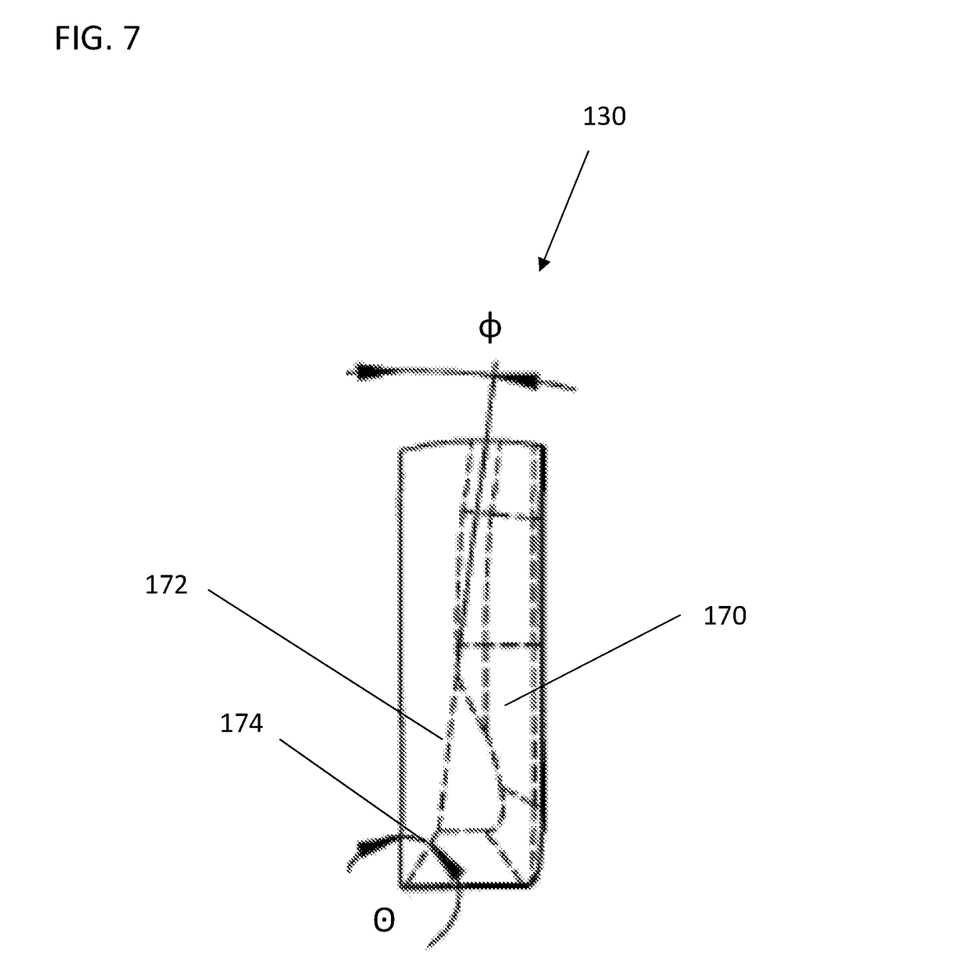
FIG. 7 is a side view of the insertion end of the inserter for a urethral plug, in accordance with disclosed embodiments.

FIG. 7 shows close up side view of the proximal insertion end 130 of a urethral plug insertion device 100. Visible in this view is the floor 172 of the central channel 170 which slopes at the proximal end at an angle φ with respect to the outside of the outside urethral plug insertion device 100. The angle φ is from about 5° to about 10°, such as about 5°, about 6°, about 7°, about 8°, about 9°, or about 10°. Also shown Also shown in this view are the plug body coupling taper 174, which makes an angle ☉ with respect to the outside of the outside urethral plug insertion device 100. The angle ☉ is from about 25° to about 35°, such as about 25°, about 26°, about 27°, about 28°, about 29°, about 30°, about 31°, about 32°, about 33°, about 34°, or about 35°.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A urethral plug inserter for inserting a urethral plug into a urethra of a male subject, the inserter comprising:
   a proximal insertion end;
   a distal gripping end;
   a central portion disposed between the proximal insertion end and the distal gripping end; and
   a central channel, comprising a floor, and axially extending from the proximal insertion end to the distal gripping end, wherein the central channel is configured to accept a lanyard section of the urethral plug, and wherein the inserter is elongate, and wherein the floor of the central channel slopes from the distal gripping end and the proximal insertion end toward a middle of the central portion and wherein a depth of the central channel is less in the middle of the central portion than a depth of the central channel at the distal gripping end and the proximal insertion end.

2. The urethral plug inserter of claim 1, wherein the proximal insertion end comprises a tapered conic section contiguous with the central channel, wherein the tapered conic section is configured to correspond to the contour of, and retain, the urethral plug.

3. The urethral plug inserter of claim 2, wherein the tapered conic section makes an angle ☉ with respect to the outside of the urethral plug insertion device and wherein the angle ☉ is from about 25° to about 35°.

4. The urethral plug inserter of claim 1, wherein the distal gripping end comprises protruding ridges on an exterior surface configured to provide grip to a user.

5. The urethral plug inserter of claim 1, wherein the distal gripping end comprises a urethral plug stopper retention system.

6. The urethral plug inserter of claim 5, wherein the urethral plug stopper retention system comprises a first set of urethral plug location protrusions and a second set of urethral plug location protrusions separated by, and disposed on either side of, a urethral plug location slot.

7. The urethral plug inserter of claim 6, wherein the first set of urethral plug location protrusions protrudes further than the second set of urethral plug location protrusions.

8. The urethral plug inserter of claim 1, wherein the central portion comprises two or more depth indicators, configured to provide information about the insertion depth of the urethral plug inserter in the urethra of the male subject.

9. The urethral plug inserter of claim 1, wherein the central portion has a smooth outer surface.

10. The urethral plug inserter of claim 1, wherein the outer surface has a surface finish ranging from about A-2 to about C-1.

11. The urethral plug inserter of claim 1, wherein the proximal insertion end, the distal gripping end, and the central portion are a unitary body of continuous material.

12. The urethral plug inserter of claim 1, wherein the proximal insertion end, the distal gripping end, and the central portion comprise a polymer.

13. The urethral plug inserter of claim 1, wherein the inserter has a fixed maximum diameter of 3 to 15 mm.

14. The urethral plug inserter of claim 1, wherein the inserter has a fixed maximum length of about 100 to about 130 mm.

15. A method of controlling urinary incontinence comprising:
   introducing the urethral plug inserter of claim 1 into a urethra of a male subject; and positioning the urethral plug in the male subject's urethra.

16. A urethral plug inserter for inserting a urethral plug into a urethra of a male subject, the inserter comprising:
   a proximal insertion end;
   a distal gripping end;
   a central portion disposed between the proximal insertion end and the distal gripping end; and
   a central channel, comprising a floor, and axially extending from the proximal insertion end to the distal gripping end, wherein the central channel is configured to accept a lanyard section of the urethral plug, and wherein the inserter is elongate, and wherein the proximal insertion end comprises a tapered conic section contiguous with the central channel, wherein the tapered conic section is configured to correspond to the contour of, and retain, the urethral plug.

17. The urethral plug inserter of claim 16, wherein the tapered conic section makes an angle ☉ with respect to the outside of the urethral plug insertion device and wherein the angle ☉ is from about 25° to about 35°.

18. The urethral plug inserter of claim 16, wherein the distal gripping end comprises protruding ridges on an exterior surface configured to provide grip to a user.

19. The urethral plug inserter of claim 16, wherein the distal gripping end comprises a urethral plug stopper retention system.

20. The urethral plug inserter of claim 19, wherein the urethral plug stopper retention system comprises a first set of urethral plug location protrusions and a second set of urethral plug location protrusions separated by, and disposed on either side of, a urethral plug location slot.

21. The urethral plug inserter of claim 20, wherein the first set of urethral plug location protrusions protrudes further than the second set of urethral plug location protrusions.

22. The urethral plug inserter of claim 16, wherein the central portion comprises two or more depth indicators, configured to provide information about the insertion depth of the urethral plug inserter in the urethra of the male subject.

23. The urethral plug inserter of claim 16, wherein the central portion has a smooth outer surface.

24. The urethral plug inserter of claim 16, wherein the outer surface has a surface finish ranging from about A-2 to about C-1.

25. The urethral plug inserter of claim 16, wherein the proximal insertion end, the distal gripping end, and the central portion are a unitary body of continuous material.

26. The urethral plug inserter of claim 16, wherein the proximal insertion end, the distal gripping end, and the central portion comprise a polymer.

27. The urethral plug inserter of claim 16, wherein the inserter has a fixed maximum diameter of 3 to 15 mm.

28. The urethral plug inserter of claim 16, wherein the inserter has a fixed maximum length of about 100 to about 130 mm.

29. A method of controlling urinary incontinence comprising:
    introducing the urethral plug inserter of claim 16 into a urethra of a male subject; and positioning the urethral plug in the male subject's urethra.

* * * * *